US006875843B2

(12) United States Patent
Jacobson

(10) Patent No.: US 6,875,843 B2
(45) Date of Patent: Apr. 5, 2005

(54) PREVENTION OF DIABETES AND PROLONGATION OF THE HONEYMOON PHASE OF DIABETES BY ADMINISTRATION OF GNRH ANTAGONISTS

(75) Inventor: Jill D. Jacobson, Kansas City, MO (US)

(73) Assignee: Children's Mercy Hospital, Kansas City, MO (US)

( * ) Notice: Subject to any disclaimer, the term of this patent is extended or adjusted under 35 U.S.C. 154(b) by 21 days.

(21) Appl. No.: 10/193,862

(22) Filed: Jul. 12, 2002

(65) Prior Publication Data

US 2003/0045475 A1 Mar. 6, 2003

Related U.S. Application Data

(63) Continuation-in-part of application No. 09/771,434, filed on Jan. 26, 2001, now abandoned.

(51) Int. Cl.[7] .................. A61K 38/24; A61K 49/00; C07K 5/00
(52) U.S. Cl. .................. 530/313; 530/328; 514/15; 424/9.1
(58) Field of Search ................ 530/313, 328; 514/15; 424/9.1

(56) References Cited

U.S. PATENT DOCUMENTS 5,480,969 A    1/1996   Bowers et al. ............ 530/328

OTHER PUBLICATIONS

Jacobson et al., Endocrinology 134, 2516–2523 (1994).*

Ansari et al., Endocrinology 145, 337–342 (2004).*

Jacobson et al., J. Allergy and Clinical Immunology 104, 653–658 (1999).*

Morale et al., Endocrinology 128, 1073–1085 (1991).*

Batticane et al., Endocrinology 129, 277–286 (1991).*

* cited by examiner

*Primary Examiner*—Jon Weber
*Assistant Examiner*—Chih-Min Kam
(74) *Attorney, Agent, or Firm*—Hovey Williams LLP

(57) ABSTRACT

A method for reducing the incidence or delaying the onset of diabetes in diabetes-susceptible mammals (e.g., mice, rats, humans) is provided wherein the mammals are treated with a gonadotropin-releasing hormone (GnRH) antagonist. Additionally, the present invention provides a method of prolonging the honeymoon phase and decreasing the rate of islet cell infiltration by lymphocytes by administration of a GnRH antagonist. Preferably, the antagonist is administered repeatedly over time by subcutaneous injection. Preferred antagonists include Acetyl-β-[2-Naphthyl]-D-Ala-D-p-Chloro-Phe-β-[3-Pyridyl]-D-Ala-Ser-Nε-[Nicotinoyl]-Lys-Nε-[Nicotinoyl]-D-Lys-Leu-Nε-[Isopropyl]-Lys-Pro-D-Ala-NH$_2$, Nal-Glu, Abarelix, Degarelix, and acetyl-D2Nal-D4ClPhe-D3Pal-Ser-Aph(Ac)-D-Aph(Ac)-Leu-Lys(lpr)-Pro-D-Ala-NH2.

15 Claims, 5 Drawing Sheets

PREVENTION OF DIABETES AND PROLONGATION OF THE HONEYMOON PHASE OF DIABETES BY ADMINISTRATION OF GNRH ANTAGONISTS

RELATED APPLICATION

This application is a continuation-in-part of application Ser. No. 09/771,434 filed on Jan. 26, 2001, now abandoned, the content and teachings of which are incorporated by reference herein.

BACKGROUND OF THE INVENTION

1. Field of the Invention

The present invention is directed to a method of reducing the incidence or delaying the onset of diabetes in diabetes-susceptible mammals by the administration to the mammal of an effective amount of a gonadotropin-releasing hormone (GnRH) antagonist. Significantly, GnRH antagonist administration is predicted to prolong the honeymoon phase of diabetes in mammals after a diagnosis of diabetes has been made. Statistically significant reductions in diabetes incidence and/or onset as well as a prolongation of the honeymoon phase of diabetes are predicted to occur after administration of such antagonists.

2. Description of the Prior Art

There are 15.7 million people (5.9% of the population) in the United States who have diabetes. An estimated 10.3 million people have been diagnosed with diabetes, while 5.4 million people are unaware that they have a disease. Each day approximately 2,200 people are diagnosed with diabetes. Diabetes is the seventh leading cause of death (sixth-leading cause of death by disease) in the United States. Diabetes is a chronic disease that has no cure. Diabetes is one of the most costly health problems in America. Health care and other costs directly related to diabetes treatment, as well as the costs of lost productivity, are believed to be $98 billion annually.

Diabetes is a disease in which the body does not produce or properly use insulin, a hormone that is needed to convert sugar, starches and other food into energy needed for daily life. The exact causes of diabetes remain a mystery, although both genetics and environmental factors such as obesity and lack of exercise appear to play roles. There are two major types of diabetes:

Type 1. An autoimmune disease in which the body does not produce any insulin, most often occurring in children and young adults. People with Type 1 diabetes must take daily insulin injections to stay alive. Type 1 diabetes accounts for 5–10 percent of diabetes.

Type 2. A metabolic disorder resulting from the body's inability to make enough, or properly use insulin. It is the most common form of the disease. Type 2 diabetes accounts for 90–95 percent of diabetes. Type 2 diabetes is nearing epidemic proportions, due to an increased number of older Americans, and a greater prevalence of obesity and sedentary lifestyles.

Type 1 diabetes results from an autoimmune process in which the body's immune system attacks and destroys the insulin producing cells of the pancreas. Because glucose cannot enter the cells, it builds up in the blood and the body's cells literally starve to death. People with Type 1 diabetes must take daily insulin injections to stay alive.

The strikingly increased incidence of certain autoimmune diseases in females compared to males is well accepted. Although there is evidence that androgens and estrogens play a role in the pathogenesis of autoimmunity, the exact roles of gonadal steroids in autoimmune diseases remain unclear. A number of studies in experimental models have shown that gonadectomy modifies the expression of autoimmune diseases, including diabetes. (Roubinian, et al., (1978) Effect of Castration and Sex Hormone Treatment on Survival, Anti-nucleic Acid Antibodies, and Glomerulonephritis in NZB/NZW F1 Mice. *J. Exp Med*, 147, 1568–83; Hawkins, et al., (1993) The Effect of Neonatal Sex Hormones on the Incidence of Diabetes in Nonobese Diabetic Mice. *Proc. Soc. Exper. Biol. Med*, 202, 201–205; Makino, et al., (1981) The Effect of Castration on the Appearance of Diabetes in Nod Mouse. *Exp Anim*, 30; and Fitzpatrick, et al., (1991) Influence of Castration, along or Combined with Thymectomy, on the Development of Diabetes in the Nonobese Diabetic Mouse. *Endocrinology*, 129, 1382–1390)

However, most studies of gender differences in autoimmunity are performed in vivo, where manipulations such as gonadectomy or administration of gonadal steroids will necessarily alter feedback effects on hypothalamic and pituitary hormones, some of which are now known to be immunomodulatory. One hypothalamic hormone with immunomodulatory properties is gonadotropin-releasing hormone (GnRH) (also known as luteinizing hormone releasing hormone (LHRH)). GnRH is known to possess indirect immunomodulatory properties via its regulation of gonadal steroids. GnRH has been shown to exert direct immunomodulatory effects in vitro and in vivo in gonadectomized rats. GnRH agonists can prevent the involution of the thymus gland which normally occurs with aging in the rat (Marchetti, et al., (1989) Luteinizing Hormone-releasing Hormone (LHRH) Agonist Restoration of Age-associated Decline of Thymus Weight, Thymic LHRH Receptors, and Thymocyte Proliferative Capacity. *Endocrinology*, 125, 1037–45). GnRH agonist administration has been associated with increases in B and T cell proliferative responses and in an increase in the number of T lymphocytes expressing the Il–2 receptor in rats (Morale, et al., (1991) Blockade of Central and Peripheral Luteinizing Hormone-releasing Hormone (LHRH) Receptors in Neonatal Rats with a Potent LHRH-antagonist Inhibits the Morphofunctional Development of the Thymus and Maturation of the Cell-mediated and Humoral Immune Responses. *Endocrinology*, 128, 1073–85; and Batticane, et al., (1991) Luteinizing Hormone-releasing Hormone Signaling at the Lymphocyte Involves Stimulation of Interleukin-2 Receptor Expression. *Endocrinology*, 129,277–86). Moreover, spleen and thymus preparations have been shown to contain mRNA for GnRH and to produce an immunoreactive GnRH (Emanuele, et al. (1990) Rat Spleen Lymphocytes Contain an Immunoactive and Bioactive Luteinizing Hormone-releasing Hormone. *Endocrinology*, 126,2482–6; and Maier, et al., (1992) Thymocytes Express a mRNA That is Identical to Hypothalamic Luteinizing Hormone-releasing Hormone mRNA. *Cell Mol Neurobiol*, 12, 447–54). A recent study demonstrates that lymphocytic GnRH production increases when T-cells are activated by PHA in vitro (Azad, et al., (1993) Immunoactivation Enhances the Concentration of Luteinizing Hormone-releasing Hormone Peptide and its Gene Expression in Human Peripheral T-lymphocytes. *Endocrinology*, 133, 215–23). Thus, GnRH appears to exert generally stimulatory effects on the immune system.

SUMMARY OF THE INVENTION

The present invention addresses the problem of mammalian diabetes by provision of a method for reducing the incidence of the ailment and/or delaying the onset thereof in at-risk mammals having a susceptibility to diabetes. Additionally, the present invention decreases the rate at which islet cells are infiltrated by lymphocytes and thereby is predicted to prolong the honeymoon phase of diabetes for mammals which have been diagnosed as having diabetes and are currently in the honeymoon phase. Broadly speaking, the method involves administration to such susceptible and diagnosed mammals of an effective amount of a GnRH antagonist. This has been found to give statistically significant decreases in development of diabetes or delays in the onset of the disease. It is predicted to prolong the honeymoon phase of diabetes by decreasing the rate at which islet cells are infiltrated. A GnRH antagonist is a substance that inhibits the relevant function of the endocrine system, the biosynthesis of GnRH, or the in vivo action of GnRH. These antagonists bind to the GnRH receptor and prevent GnRH from binding to the receptor, thereby decreasing GnRH action. This reduction in action is reflected in a reduction in serum LH levels or a reduction in the ratio of luteinizing hormone (LH) to follicle stimulating hormone (FSH). This reduction in LH levels is coupled with an attendant suppression of immune function. This inverse correlation of LH levels and immune parameters has been demonstrated in two separate animal models. In one model, a direct correlation between LH:FSH ratios, which are a measure of GnRH responsiveness, and anti-DNA antibody levels, which correlate directly with disease severity, was shown in lupus- prone mice (FIG. 1). The direct relationship between anti-DNA antibody levels in lupus-prone mice (a measure of autoimmune disease severity) with LH:FSH ratios is illustrated in FIG. 1. This demonstrates that responsiveness to GnRH increases as the severity of the illness increases. In FIG. 1, n=10 and p<0.05. In the second model, a direct correlation between T helper cell numbers (CD4 counts) and LH levels was shown in diabetes- prone BB rats (FIG. 2 in which n=14 and p<0.05). This suggests that animals which are more responsive to GnRH generate greater numbers of immune cells.

In practice, susceptible mammals and mammals which have been diagnosed with diabetes -such as mice, rats and humans can be treated in accordance with the invention. Generally, an effective GnRH antagonist is administered (usually by subcutaneous injection) repeatedly over time to achieve the best results. A -variety of known GnRH antagonists may be employed, such as Acetyl-β-[2-Naphthyl]-D-Ala-D-p-Chloro-Phe-β-[3-Pyridyl]-D-Ala-Ser-Nε-[Nicotinoyl]-Lys-Nε-[Nicotinoyl]-D-Lys-Leu-Nε-[Isopropyl]-Lys-Pro-D-Ala-NH$_2$ (also referred to herein as Antide), acetyl-D2Nal1, D4C1Phe2, D3Pal3, ARg5, Dglu6 (AA) (also referred to herein as NalGlu), acetyl-D2Nal-D4ClPhe-D3Pal-Ser-Aph(Ac)-D-Aph(Ac)-Leu-Lys(lpr)-Pro-D-Ala-NH2, Abarelix (Praecis, Waltham, Mass.), Nal-Lys, Deslorelin, Histrelin, Nafarelin (Synarel, Searle Peapack, N.J.), Ganirelix (Orgalutron/Antagon) (Organan, West Orange, N.J.), Cetrorelix I ASTA Medica AG, Frankfurt, Germany), Cetrotide, Azaline B, Acyline (Ac-D2Nal-D4Cpa-D3Pal-Ser4Aph(Ac)-D4Aph(Ac)-Leu-ILys-Pro-DAla-NH2), new generation long-acting GnRH analogues incorporating p-ureido-phenylalanines at positions 5 and 6 (such as Degarelix (Ferring, Geneva, Switzerland)), FE200486, Ac-D2Nal-D4Cpa-D3Pal-Ser-4Aph(L-hydroorotyl)-D4Aph(carbarnoyl)-Leu-ILys-Pro-DAla-NH2 (the acetate salt of which is FE200486), Ac-D2Nal-D4Cpa-D3Pal-Ser-4Aph(Atz)-D4Aph(Atz)-Leu-ILys-Pro-DAla-NH2 wherein Atz is 3'-amino-1H-1',2',4'-triazol-5'-yl,5, the antagonists described in U.S. Pat. Nos. 5,434,136, 6,156,772, 6,156,767, 6,150,522, 6,150,522, 6,150,352, 6,147,088, 6,077,858, 6,077,847, 6,025,366, 6,017,944, 6,004,984, 5,998,432, and a novel and potent GnRH antagonist which induces a rapid and profound prostate gland volume reduction (PGYR) and androgen suppression before brachytherapy (BT) or radiation therapy (XRT), *Poster Sessions*, Endo '98, p. 265 (the content and teachings of this article and the referenced patents are hereby incorporated by reference) could be used to practice the present invention. GnRH antagonists useful in the present invention will have a binding affinity that parallels the antagonistic properties and can be linear or cyclized pentapeptides to decapeptides. Of the linear peptide antagonists, peptides with large substitutions in position 6, such as those found in Degarelix, or with large substitutions such as iodinated substitutions, lead to high binding affinity. It is presently believed that Abarelix or Degarelix will be the GnRH antagonist of choice.

As used herein, a "diabetes-susceptible mammal" refers to a mammal having a statistically significant predisposition to contract Type I (autoimmune) diabetes, as compared with the normal, non-susceptible population. Such a predisposition can be ascertained using a number of genetic and/or antibody screens or tests. For example, a diabetes-susceptible human would generally exhibit at least one, and preferably two or more, of the following enumerated risk categories. A susceptible human would range in age from 0–45 years, and:

1. Be a sibling, offspring or a second or third degree relative (e.g., niece, nephew, aunt, uncle, cousin, grandchild) of a person who suffered from Type I diabetes; or
2. Have a titre of islet cell autoantibodies (ICA) greater than 10 Juvenile Diabetes Foundation (JDF) Units; or
3. Exhibit in a serum screening sample the presence of insulin autoantibodies.

As used herein, the "honeymoon phase" refers to the period of time after a mammal is diagnosed as having diabetes wherein some beta cells have been destroyed but glucose levels improve to normal or near normal levels due to the functioning of the remaining (non-destroyed) beta cells. It is estimated that at the time of diagnosis of Type I diabetes, approximately 85% of the insulin producing beta cells in the pancreas have undergone autoimmune destruction but the remaining 15% of the beta cells are capable of producing insulin. Once insulin therapy is instituted, the remaining beta cells have some of their functionality restored and glucose levels can improve to normal or near normal levels for weeks, months, or occasionally years and it is this time period that is referred to as the "honeymoon phase."

DETAILED DESCRIPTION OF THE PREFERRED EMBODIMENT

Figure 1:
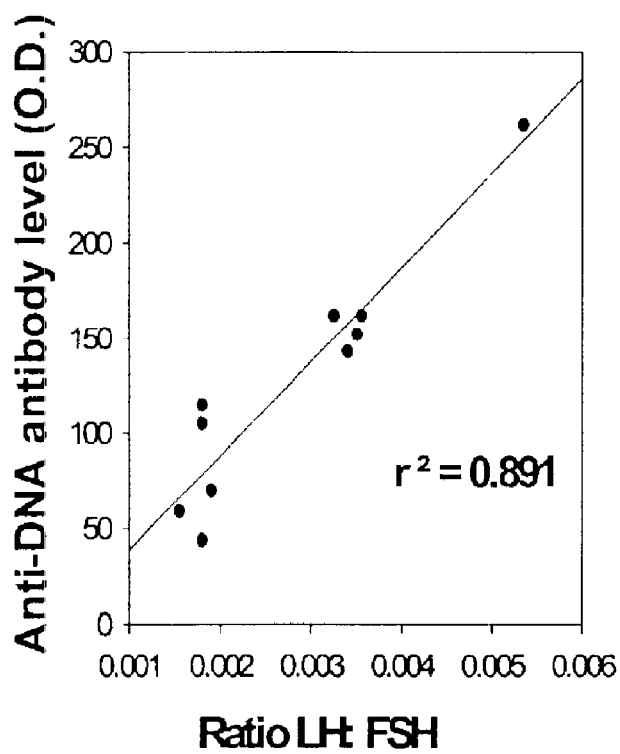
FIG. 1 illustrates the direct relationship between anti-DNA antibody levels in lupusprone mice (a measure of severity of autoimmune disease) with LH:FSH ratios.

The following examples set forth a series of tests using diabetes-susceptible mice where the mice were treated using a known GnRH antagonist. It is to be understood that these examples are provided by way of illustration and nothing therein should be taken as a limitation upon the overall scope of the invention.

EXAMPLE 1

In this example, intact and gonadectomized non-obese mouse model of diabetes (NOD mouse) mice were treated with GnRH agonists and antagonists to determine the effect thereof on serum IgG levels and the incidence and onset of diabetes.

Methods

Mice. The well-characterized NOD mice were used throughout the study. Male and female mice were purchased from the Jackson Laboratory (Bar Harbor, Me.). These mice are art-recognized animal models used in diabetes research. (Makino et al., (1980) Breeding of a Non-obese Diabetic Strain of Mice. *Exp Anim*, 29, 1–13; Miyazaki, A. T., et al, (1985) Predominance of T Lymphocytes in Pancreatic Islets and Spleen in Prediabetic Non-Obese Diabetic (Nod) Mice: a Longitudinal Study. *Clin Exp immunol*, 60, 622–630)

Experimental Design. Both intact and gonadectomized mice (GDX) were used. Gonadectomies were performed to demonstrate an increase in the incidence of diabetes and also order to eliminate the variable of sex hormone production. To compare the effects of GnRH agonists and antagonists, gonadectomized animals were randomized at 14 to 18 days of age and begun immediately in one of the following main treatment groups: GnRH agonist; Antide; vehicle. One group of gonadectomized males was treated with Nal-Glu, as an additional control.

Data from mice born over a period of several-weeks and randomized to treatment or control groups in several different batches were combined. Serum collection was staggered so that all mice were bled at the same 4 week intervals. Sera for antibody measurements were stored at −20° C., and all samples from each time-point were run in the same assay in an effort to avoid interassay variability.

Gonadectomy. Males were gonadectomized via a single scrotal incision under pentobarbital anesthesia.

Sham operated males underwent pentobarbital anesthesia and a scrotal incision.

Injections. GnRH (native decapeptide) was purchased from Bachem (Bubendorf, Switzerland). GnRH antagonist Antide (Acetyl-β-[2-Naphthyl]-D-Ala-D-p-Chloro-Phe-β-[3-Pyridyl]-D-Ala-Ser-Nε-[Nicotinoyl]-Lys-Nε-[Nicotinoyl]-D-Lys-Leu-Nε-[Isopropyl]-Lys-Pro-D-Ala-$NH_2$) was supplied by Contraceptive Development Branch (NICHHD) of the National Institutes of Health and Ares-Serono (Randolph, Mass.). A second GnRH antagonist, Nal-Glu (acetyl-D2Nal1, D4ClPhe2, D3Pal3, Arg5, Dglu6 (AA), DAla10) was supplied by NICHHD and was used on a subset of mice. All references to GnRH agonist refer to the native decapeptide. Animals were injected subcutaneously in the nape of the neck six times weekly, in the a.m., with 100 μg of GnRH or GnRH antagonist in 100 μl of vehicle consisting of 50% propylene glycol and 50% double distilled water.

Sera. Sera were collected from blood obtained every six weeks by retroorbital puncture after light isofluorane anesthesia.

Hormone measurements. Serum testosterone concentrations were measured by RIA using a commercial kit (Coat-A-Count, Diagnostic Products Corporation, Los Angeles, Calif.). Serum LH and prolactin were measured by radioimmunoassay (RIA) using previously described methods. (Neill, J. D. et al. (1971) Development of a radioimmunoassay for rat prolactin and evaluation of the NIAMD rat prolactin radioimmunoassay. *Endocrinology*, 88, 548–55; Niswender, et al. (1968) Radioimmunoassay for Rat Luteinizing Hormone with Antiovine Lh Serum and Ovine Lh-131-i. *Proc Soc Exp Biol Med*, 128, 807–11.

Clinical tests. Total immunoglobulin G concentrations were measured by single radial immunodiffusion assay using immunodiffusion plates containing monospecific antiserum for IgG (ICN Biomedicals, Inc., Costa Mesa, Calif.). Serum glucoses were checked weekly using a One Touch Fast Take meter (Lifescan, Milpitas, Calif.) Urine was tested for glucose by urinalysis reagent strips (Miles, Inc., Elkhart Ind.). Glycosuria was scored by comparison to reference standards on a scale of 0 to 4 as follows: negative=0; 30 mg/dL=1; 100 mg/dL=2; 300 mg/dL=3;>1000 mg/dL=4.

Necropsies. Necropsies were performed on representative mice. No residual ovarian or testicular tissue was found.

Statistics. Serum immunoglobulin measurements were compared by two-tailed Student's paired t-tests. Percentages of mice remaining diabetes-free was assessed by Mantel-Haenszel methodology. (Mantel, N. (1966) Evaluation of Survival Data and Two New Rank Order Statistics Arising in its Consideration. *Cancer Chemother Rep*, 50, 163–70)

Results

Figure 3:
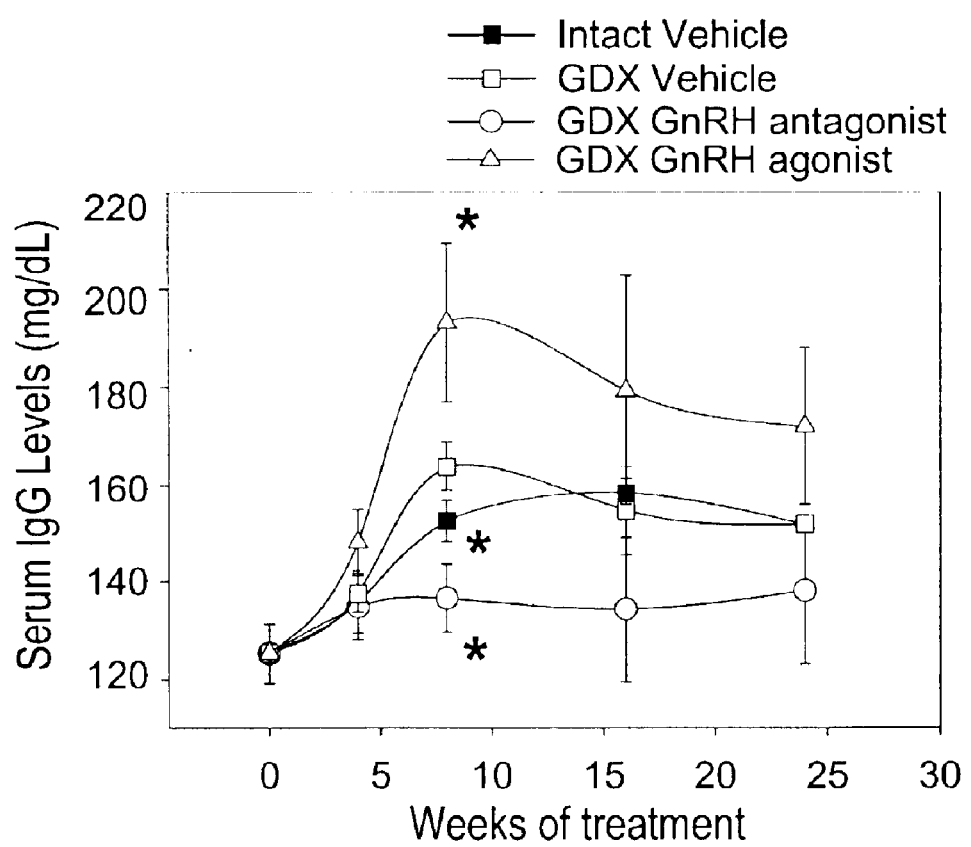
FIG. 3 is a graph illustrating the effects of GnRH, a GnRH antagonist and a GnRH agonist on IgG levels in gonadectomized and sham gonadectomized-NOD mice.

Serum Immunoglobulin G concentrations. Gonadectomy significantly increased IgG levels compared to sham gonadectomy after 8 weeks of treatment. Treatment of gonadectomized mice with GnRH agonist further increased IgG levels compared to vehicle. In gonadectomized males, Antide treatment reduced serum IgG concentrations to levels seen in sham operated mice at 8 weeks. The data for this example is shown in FIG. 3. As shown by FIG. 3, GnRH antagonist treatment is associated with a statistically significant reduction in serum IgG levels ($p<0.05$, n=8–27/treatment group).

Figure 4:
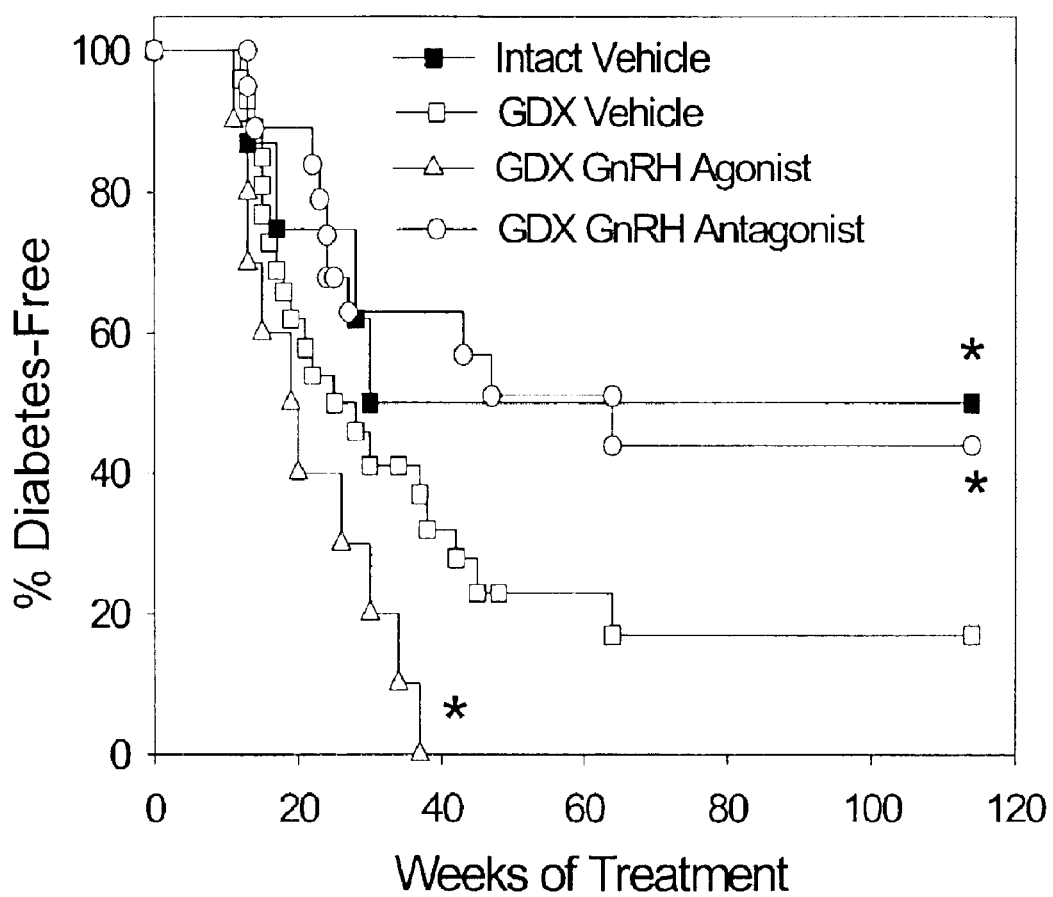
FIG. 4 is a graph illustrating the effect of GnRH antagonist, vehicle and GnRH agonists upon the timing and incidents of diabetes in gonadectomized and sham gonadectomized male NOD mice (percentage diabetes-free mice versus time in weeks); and, FIG. 5 is a graph illustrating the decreased rate of islet infiltration in gonadectomized mice after treatment with a GnRH antagonist or vehicle.

Incidence of diabetes. In gonadectomized males, the incidence of diabetes was significantly decreased by administration of the GnRH antagonist Antide. At 60 weeks of age 0% of Antide treated mice were diabetic compared to vehicle ($p=0.0025$, n=8–27/treatment group; FIG. 4).

As shown in FIG. 4, GnRH agonist treatment significantly increased the incidence and accelerated the timing of onset of diabetes.

EXAMPLE 2

In this example, gonadectomized NOD mice were treated with either the GnRH antagonist Antide or the vehicle (50% propylene glycol and 50% double distilled water) to determine differences in the rate of lymphocytic infiltration of islet cells.

Methods

Mice. The well-characterized NOD mice were used throughout the study. Male and female mice were purchased from the Jackson Laboratory (Bar Harbor, Me.). Again, these mice are art-recognized animal models used in diabetes research.

Gonadectomy. Males were gonadectomized via a single scrotal incision under pentobarbital anesthesia.

Injections. The mice were injected subcutaneously in the nape of the neck six times weekly, in the a.m., with 100 µg of the GnRH antagonist in 100 µl of vehicle consisting of 50% propylene glycol and 50% double distilled water.

Pancreatic Histology. Three mice per treatment group were euthanized at 3, 5, 7, 9, and 11 weeks. Pancreatic histologic sections were stained by hemotoxillin and eosin. Ten tissue sections per treatment group were examined. All beta cells in each tissue section were scored with regard to the presence or absence of lymphocytic infiltrates.

Results

Figure 5:
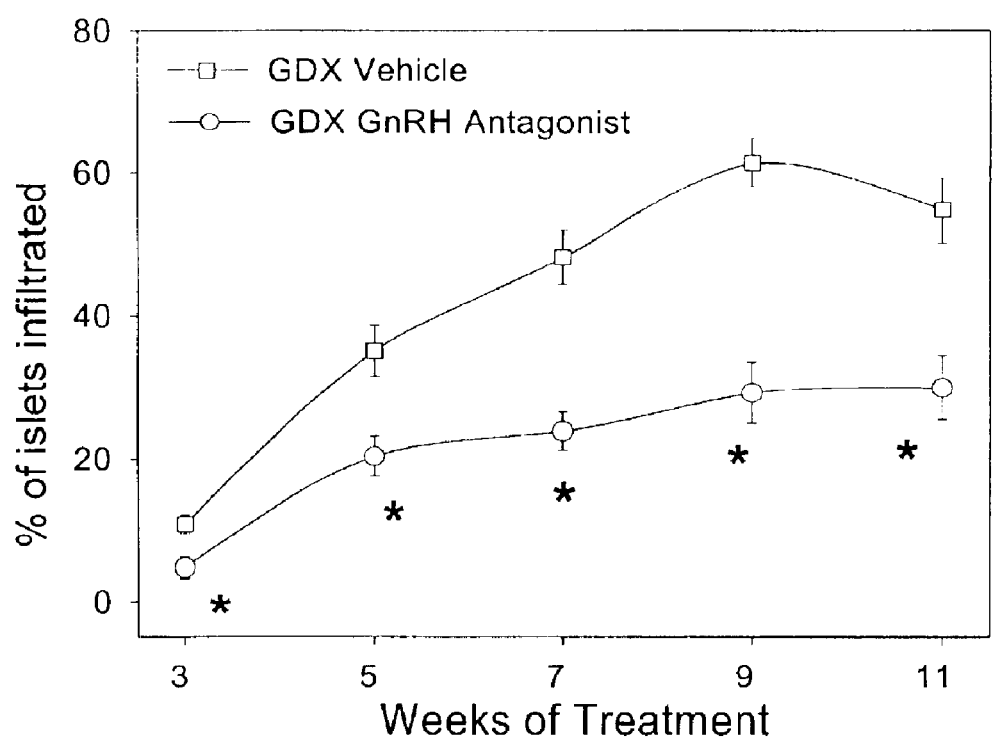

Islet Cell Infiltration. GnRH administration was associated with a significant reduction in percentages of islets infiltrated at all time points examined. Results of this experiment are given in FIG. 5. As shown in FIG. 5, GnRH antigonist treatment is associated with a statistically significant reduction in lymphocytic infiltration ($p<0.05$).

Discussion

One goal of this study was to determine whether a reduction in GnRH activity was associated with an amelioration of diabetes in gonadectomized male mice susceptible to diabetes. No attempt was made to distinguish hypothalamic versus pituitary hormone effects; likewise, no attempt was made to determine the relative importance of gonadal hormones versus hypothalamic/pituitary hormones. Nevertheless, the first Example confirms that -GnRH and/or its pituitary products appear to modify the expression of murine diabetes, and raise the hypothesis that hormones other than gonadal steroids might contribute to the well-known gender differences in expression of autoimmunity.

In Example 1, gonadectomized mice were studied in order to eliminate the actions of GnRH on gonadal steroid production as well as gonadal feedback effects on GnRH release. This allowed a more direct assessment of the role of GnRH in modulating murine diabetes. It was found that gonadectomized NOD mice treated with GnRH antagonist displayed statistically significant decreases in total IgG, and delayed onset of diabetes. GnRH agonist administration resulted in reciprocal effects.

GnRH antagonists might act on the immune system directly, by a direct effect on B or T lymphocytes, or indirectly, either by a reduction in gonadotropins or in cytokine production by immune cells. The prior art suggests that GnRH agonists may play a role in both B and T cell proliferation in vivo and in vitro (Marchetti, B., et al., (1989) Luteinizing Hormone-releasing Hormone (LHRH) Agonist Restoration of Age-associated Decline of Thymus Weight, Thymic LHRH Receptors, and Thymocyte Proliferative Capacity. Endocrinology, 125,1037–45; Morale, M. C., et al., (1991) Blockade of Central and Peripheral Luteinizing Hormone-releasing Hormone (LHRH) Receptors in Neonatal Rats with a Potent LHRH-antagonist Inhibits the Morphofunctional Development of the Thymus and Maturation of the Cell-mediated and Humoral Immune Responses. Endocrinology, 128, 1073–85; and Batticane, N., et al., (1991) Luteinizing Hormone-releasing Hormone Signaling at the Lymphocyte Involves Stimulation of Interleukin-2 Receptor Expression. Endocrinology, 129, 277–86). For example, work demonstrating previous decreased percentages of B lymphocytes in gonadectomized lupus-prone mice treated with GnRH antagonists suggests that GnRH antagonists in some way interfere with B lymphocyte proliferation. A decrease in B lymphocyte proliferation could explain the observed reduction in serum IgG and autoantibody concentrations and in decreased immune complex-mediated renal disease.

Inhibition of prolactin release has been shown to decrease disease severity and prolong survival in murine diabetes, whereas prolactin therapy exacerbates disease. (McMurray, R., et al., (1991) Prolactin Influences Autoimmune Disease Activity in the Female B/w Mouse. J Immunol, 147, 3780–7) However, it was found that neither agonist nor antagonist treatment altered serum prolactin levels. Thus, it is believed that the observed effects were independent of prolactin.

Previous reports have documented the ability of estradiol to exacerbate murine diabetes. Although the feedback effects of estradiol on GnRH are complex, it is known that estradiol exerts positive feedback effects on GnRH production in some circumstances. Estradiol has been shown to increase GnRH release from hypothalamic cells in vitro. (Leadem, C. A. et al., (1984) Stimulation with Estrogen and Progesterone of Luteinizing Hormone (LH)-releasing Hormone Release from Perifused Adult Female Rat Hypothalami: Correlation with the Lh Surge. Endocrinology, 114, 51–6. A rise estradiol is believed to contribute to the midcycle GnRH surge. (Roselli, C. E. et al. (1990) Regulation of Hypothalamic Luteinizing Hormone-releasing Hormone Levels by Testosterone and Estradiol in Male Rhesus Monkeys. Brain Res, 509, 343–6) An estrogen response element with positive regulatory effects has been identified on the 5' side of the GnRH gene. (Radovick, S., et al. (1991) Evidence for Direct Estrogen Regulation of the Human Gonadotropin-releasing Hormone Gene. J Clin Invest, 88, 1649–55) Based on these observations, it is possible that some of the immunostimulatory actions of estradiol may result from its positive feedback on GnRH.

Androgens have been shown to negatively regulate GnRH and gonadotropin production and release. (Finkelstein, J. S., et al. (1991) Sex Steroid Control of Gonadotropin Secretion in the Human Male. I. Effects of Testosterone Administration in Normal and Gonadotropin-releasing Hormone-deficient Men. J Clin Endocrinol Metab, 73, 609–20; Veldhuis, J. D., et al. (1992) Evidence That Androgen Negative Feedback Regulates Hypothalamic Gonadotropin-releasing Hormone Impulse Strength and the Burst-like Secretion of Biologically Active Luteinizing Hormone in Men. J Clin Endocrinol Metab, 74, 1227–35; and Kalra, P. S. et al. (1982) Discriminative Effects of Testosterone on Hypothalamic Luteinizing Hormone-releasing Hormone Levels and Luteinizing Hormone Secretion in Castrated Male Rats: Analyses of Dose and Duration Characteristics. Endocrinology, 111, 24–9). They have also been shown to exert suppressive actions in autoimmunity: androgen treatment ameliorates murine diabetes, whereas gonadectomy of males exacerbates the disease. (Hawkins, T., et al. (1993) The Effect of Neonatal Sex Hormones on the Incidence of Diabetes in Nonobese Diabetic Mice. Proc. Soc. Exper. Biol. Med., 202, 201–205; Makino, S., et al. (1981) The Effect of Castration on the Appearance of Diabetes in NOD Mouse. Exp Anim, 30; Fitzpatrick, F., et al. (1991) Influence of Castration, along or Combined with Thyrmectomy, on the Development of Diabetes in the Non-obese Diabetic Mouse. Endocrinology, 129,1382–1390. Various preparations of androgen have been used with success in human autoimmune disorders such as lupus and ITP. (Bizzarro, A., et al. (1987) Influence of Testosterone Therapy on Clinical and Immunological Features of Autoimmune Diseases Associated with Klinefelter's Syndrome. J Clin Endocrinol Metab, 64, 32–6; and Weinblatt, M. E., et al. (1988) Danazol for Children with Immune Thrombocytopenic Purpura. Am J Dis Child, 142, 1317–9).

Figure 2:
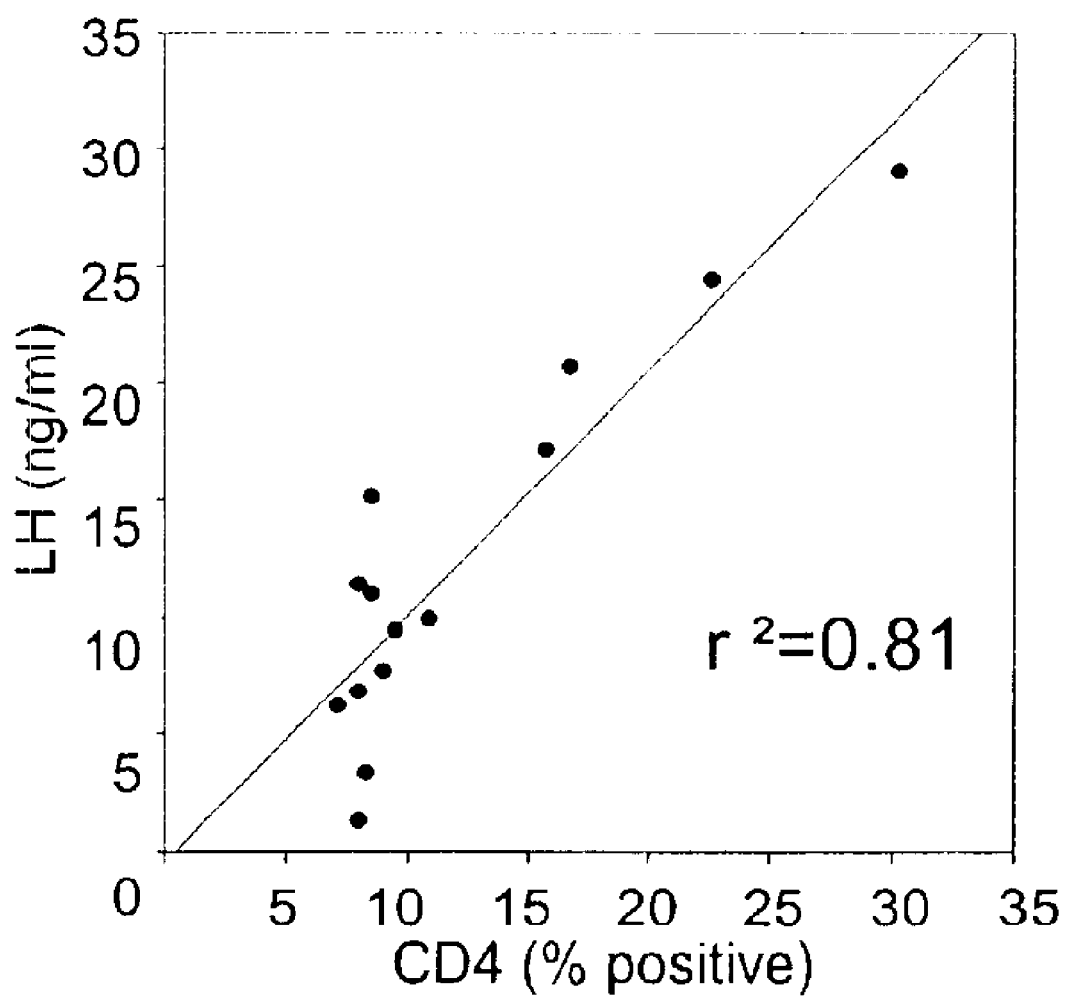
FIG. 2 demonstrates the direct relationship between LH levels and T helper cell (CD4) numbers.

These examples demonstrate that GnRH antagonists exert immunomodulatory actions in diabetes. As illustrated in FIG. 2, GnRH antagonists significantly increases the number of diabetes-free mice over the test period. Taken together, these studies confirm that GnRH antagonists modulate the expression of murine diabetes independently of their effects on the gonads. Thus, it establishes that GnRH agonists and antagonists exert immune actions which are distinct from those of androgens and estrogens.

Another goal of this experiment was to determine the likelihood whether the honeymoon phase of diabetes could be prolonged by the administration of a GnRH antagonist. Prolongation of the honeymoon phase would allow those animals which have been diagnosed with diabetes to extend the time in which their own islet cells produce enough insulin to maintain normal or near normal glucose levels without additional insulin therapy. Because lymphocyte infiltration of all remaining healthy islets is required to end the honeymoon phase (which will lead to permanent diabetes) we assessed whether GnRH antagonists exerts effects on lymphocyte infiltration. As shown by FIG. 3, GnRH antagonist administration was associated with a significant reduction in the percentages of islet cells infiltrated by lymphocytes at all time points of the study. Thus, it is predicted that the honeymoon phase would be extended as a greater percentage of islet cells remain functional for a greater length of time based upon the fact that fewer cells were infiltrated by lymphocytes.

All patents and literature references cited herein are expressly incorporated by reference into the specification.

I claim:

1. A method of delaying the onset of Type I diabetes in a diabetes-susceptible mammal comprising the step of administering to the mammal an effective amount of a gonadotropin-releasing hormone antagonist selected from the group consisting of Acetyl-β-2-Naphthyl-D-Ala-D-p-Chloro-Phe-β-3-Pyridyl-D-Ala-Ser-Nϵ-Nicotinoyl-Lys-Nϵ-Nicotinoyl-D-Lys-Leu-Nϵ-Isopropyl-Lys-Pro-D-Ala-NH$_2$, Abarelix, Nal-Glu, Deslorelin, Histrelin, Nafarelin, Ganirelix, Cetrorelix or the acetate salt thereof, Azaline B, and Degarelix or the acetate salt thereof, wherein said administration results in said mammal having a delayed onset of diabetes.

2. The method of claim 1, including the step of administering said antagonist by subcutaneous injection.

3. The method of claim 1, including the step of repeatedly administering said antagonist.

4. The method of claim 1, said mammal being a mouse.

5. The method of claim 1, said antagonist selected from the group consisting of Acetyl-β-2-Naphthyl-D-Ala-D-p-Chloro-Phe-β-3-Pyridyl-D-Ala-Ser-Nϵ-Nicotinoyl-Lys-Nϵ-Nicotinoyl-D-Lys-Leu-Nϵ-Isopropyl-Lys-Pro-D-Ala-NH$_2$, Nal-Glu, Abarelix, and Degarelix.

6. A method of prolonging the honeymoon phase of Type I diabetes in a diabetes-susceptible mammal comprising the step of administering to the mammal in need of, an effective amount of a gonadotropin-releasing hormone antagonist selected from the group consisting of Acetyl-β-2-Naphthyl-D-Ala-D-p-Chloro-Phe-β-3-Pyridyl-D-Ala-Ser-Nϵ-Nicotinoyl-Lys-Nϵ-Nicotinoyl-D-Lys-Leu-Nϵ-Isopropyl-Lys-Pro-D-Ala-NH$_2$, Abarelix, Nal-Glu, Deslorelin, Histrelin, Nafarelin, Ganirelix, Cetrorelix or the acetate salt thereof, Azaline B, and Degarelix or the acetate salt thereof, wherein said administration results in a prolonged honeymoon phase.

7. The method of claim 6, including the step of administering said antagonist by subcutaneous injection.

8. The method of claim 6, including the step of repeatedly administering said antagonist.

9. The method of claim 6, said mammal being a mouse.

10. The method of claim 6, said antagonist selected from the group consisting of Acetyl-β-2-Naphthyl-D-Ala-D-p-Chloro-Phe-β-3-Pyridyl-D-Ala-Ser-Nϵ-Nicotinoyl-Lys-Nϵ-Nicotinoyl-D-Lys-Leu-Nϵ-Isopropyl-Lys-Pro-D-Ala-NH$_2$, Nal-Glu, Abarelix, and Degarelix.

11. A method of reducing the rate of islet cell infiltration by lymphocytes in a diabetes-susceptible mammal comprising the step of administering to the mammal in need of, an effective amount of a gonadotropin-releasing hormone antagonist selected from the group consisting of Acetyl-β-2-Naphthyl-D-Ala-D-p-Chloro-Phe-β-3-Pyridyl-D-Ala-Ser-Nϵ-Nicotinoyl-Lys-Nϵ-Nicotinoyl-D-Lys-Leu-Nϵ-Isopropyl-Lys-Pro-D-Ala-NH$_2$, Abarelix, Nal-Glu, Deslorelin, Histrelin, Nafarelin, Ganirelix, Cetrorelix or the acetate salt thereof, Azaline B, and Degarelix or the acetate salt thereof, wherein said administration results in a reduced rate of islet cell infiltration.

12. The method of claim 11, including the step of administering said antagonist by subcutaneous injection.

13. The method of claim 11, including the step of repeatedly administering said antagonist.

14. The method of claim 11, said mammal being a mouse.

15. The method of claim 11, said antagonist selected from the group consisting of Acetyl-β-2-Naphthyl-D-Ala-D-p-Chloro-Phe-β-3-Pyridyl-D-Ala-Ser-Nϵ-Nicotinoyl-Lys-Nϵ-Nicotinoyl-D-Leu-Nϵ-Isopropyl-Lys-Pro-D-Ala-NH$_2$, Nal-Glu, Abarelix, and Degarelix.

* * * * *